United States Patent [19]

Le Clef et al.

[11] Patent Number: 4,789,587
[45] Date of Patent: Dec. 6, 1988

[54] (1,3-DIOXOLAN-2-YL-METHYL)-1H-IMIDAZOLES AS BACTERICIDAL AND/OR FUNGICIDAL AGENTS

[75] Inventors: Brigitte A. L. G. M. J. Le Clef, Louvain-la-Neuve; Ruth Laub, Bruxelles; Yves-Jacques E. Schneider, Overijse, all of Belgium

[73] Assignee: IRE-Celltarg, S.A., Fleurus, Belgium

[21] Appl. No.: 10,438

[22] Filed: Feb. 3, 1987

[30] Foreign Application Priority Data

Feb. 4, 1986 [FR] France ............... 86 01496

[51] Int. Cl.⁴ ............ A61K 31/495; A61K 31/41; A61K 31/415; C07D 405/14
[52] U.S. Cl. .................. 514/252; 544/367; 544/370
[58] Field of Search ............. 544/367, 370; 514/252

[56] References Cited

U.S. PATENT DOCUMENTS

| 4,144,346 | 3/1979 | Heeres et al. | 544/370 |
| 4,335,125 | 6/1982 | Heeres et al. | 544/370 |
| 4,391,805 | 7/1983 | Blume et al. | 544/370 |
| 4,503,055 | 3/1985 | Heeres et al. | 544/370 |
| 4,634,700 | 1/1987 | Schickaneder et al. | 544/367 |

FOREIGN PATENT DOCUMENTS

| 0006722 | 1/1980 | European Pat. Off. . |
| 0050298 | 4/1982 | European Pat. Off. . |
| 3410070 | 10/1985 | Fed. Rep. of Germany | 544/370 |
| 1037783 | 2/1986 | Japan | 544/370 |

OTHER PUBLICATIONS

Inke S. A., CA97-163020y.
Heeres et al, CA98-27336z.
Yoneyama et al, CA103-19704z.

Primary Examiner—Donald G. Daus
Assistant Examiner—Cecilia Shen
Attorney, Agent, or Firm—Fleit, Jacobson, Cohn & Price

[57] ABSTRACT

The present invention relates to compounds of formula

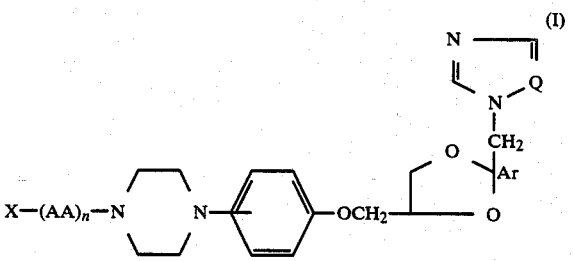

in which
Q is N or CH,
Ar is a radical chosen from among phenyl and optionally substituted thienyl radicals, it being possible for the substituents to be from one to three substituents: halo, lower alkyl or lower alkoxy,
—AA— represents a divalent radical corresponding to an amino acid forming part of the structure of proteins, it being possible for some functional groups of this radical to be protected, or alternatively, it represents a diacyl radical,
n is an integer from 0 to 4 inclusive, and
X represents H, OH or Y,

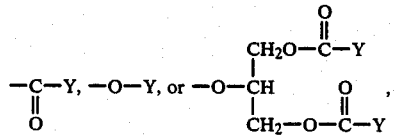

in which
when n is equal to 1, 2, 3 or 4, Y is then a hydrocarbon radical containing from 1 to 20 carbon atoms,
when n is equal to 0, Y is then a hydrocarbon radical containing from 7 to 20 carbon atoms, as well as to the salts and the isomers of these compounds, to a process for the preparation of these compounds, to their application as fungicidal and/or bactericidal agents and to their compositions containing them.

5 Claims, No Drawings

(1,3-DIOXOLAN-2-YL-METHYL)-1H-IMIDAZOLES AS BACTERICIDAL AND/OR FUNGICIDAL AGENTS

The present invention relates to (1,3-dioxolan-2-ylmethyl)-1H-imidazole derivatives which have fungicidal and bactericidal properties, to a process for the preparation thereof, to intermediates of synthesis of these compounds and to bactericidal and/or fungicidal compositions containing these derivatives.

More particularly, these are compounds of formula:

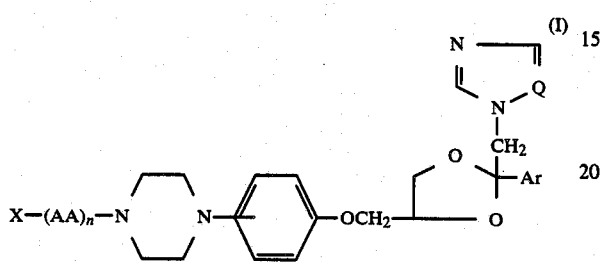

in which
Q is N or CH;
Ar is a radical chosen from amongst phenyl and optionally substituted thienyl radicals, it being possible for the substituents to be from one to three substituents: halo, lower alkyl or lower alkoxy groups;
—AA— represents a divalent radical corresponding to an amino acid forming part of the structure of proteins, it being possible for some functional groups of this radical to be protected, or alternatively, it represents a diacyl radical;
n is an integer from 0 to 4 inclusive; and
X represents H, OH or Y,

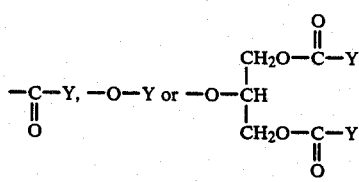

in which
when n is equal to 1, 2, 3 or 4, Y is then a hydrocarbon radical containing from 1 to 20 carbon atoms,
when n is equal to 0, Y is then a hydrocarbon radical containing from 7 to 20 carbon atoms, and the salts and the isomers of these compounds.

The compounds according to the invention differ from known derivatives of ketoconazole by their substituent in position 1 of the piperazine group.

These are especially compounds of formula Ia:

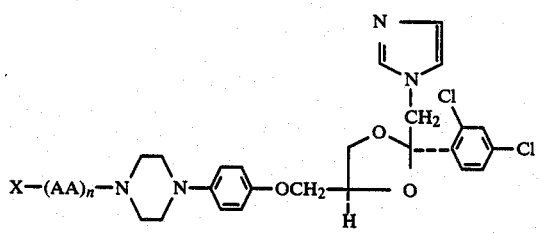

in which
—AA— represents

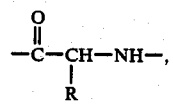

in which R represents side-chain substituents in the α position to the amino group of amino acids or the radical diacyl—succ;
n represents an integer from 0 to 4 inclusive;
X represents H, OH, Y,

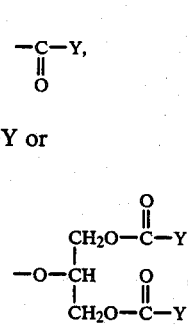

in which
Y represents a $C_7$ to $C_{20}$ hydrocarbon radical, an alkyl radical or an alkenyl radical, and —succ represents the radical

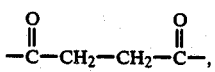

and when n≠0, Y may then be lower alkyl radical, their pharmaceutically acceptable salts and their isomeric forms.

In the present description, the lower alkyl and alkoxy radicals contain from 1 to 6 carbon atoms and preferably from 1 to 3 carbon atoms. The term "halo" represents the radicals derived from halogens, fluoro, chloro, bromo and iodo and the trifluoromethyl radical.

The divalent radicals —AA— corresponding to an amino acid forming part of the structure of proteins may come from an amino acid in the D-form or in the L-form, if there is an asymmetric carbon atom. The radical —AA— is attached to the piperazine radical preferably via its C-terminal end and the radical X is preferably attached on the N-terminal end. When the radical —AA— contains other groups, for example —OH, —NH₂ or —COOH, the latter may be free or protected by a radical Pr known in protein chemistry, for example Cbz.

The biradicals —AA— as defined represent all the biradicals derived from amino acids, viz. neutral and hydrophobic amino acids such as: glycine, alanine, valine, leucine, isoleucine, phenylalanine, proline and methionine, neutral and polar amino acids such as: serine, threonine, tyrosine, tryptophan, asparagine, glutamine and cysteine, but also the basic amino acids such as: lysine, arginine and histidine, and acids such as aspartic acid and glutamic acid.

The divalent radical —AA— may also be a diacyl radical originating from an alkanedioic or alkenedioic diacid containing from 3 to 10 carbon atoms and, if required, substituents such as, for example, succinic or maleic acids.

When n is equal to 2, 3 or 4, the radicals —AA— may then be identical or different. According to the invention, n is preferably equal to 0, 1 or 2.

Among the hydrocarbon radicals represented by Y, alkyl, alkenyl and alkynyl radicals, which may be substituted if required, should be mentioned. These radicals may be straight-chained or branched and the alkenyl radicals may contain one or more double bonds.

When the radical Y contains more than 7 carbon atoms, it is preferably the radical originating from a natural fatty acid Y—COOH, for example myristic, palmitic, stearic, oleic, linoleic and arachidic acids.

Among the compounds of formula Ia, there should be mentioned compounds in which:
n=0, $$X = -\overset{\underset{\parallel}{O}}{C}-Y,$$

Y being derived from a fatty acid,
n=1, 2,
X=OH and the substituent in position 1 is —AA—succ—
—AA— being derived from Ala or Gly,
n=1

$$X = -\overset{\underset{\parallel}{O}}{C}-Y,$$

Y being derived from a fatty acid, and
R=H or CH₃.

The carbon atoms 2 and 4 of the dioxolane ring are asymmetric, and are therefore the centres of stereoisomerism.

The present invention relates to all the stereoisomeric forms of the compounds of formula I, but especially to compounds which have a cis configuration.

The present invention also relates to pharmaceutically acceptable salts of the compounds of formula I, for example their addition salts with acids or bases.

The present invention also relates to a process for the preparation of the compound of formula I, defined in that a compound of formula:

II is reacted with an acid of formula

X—(AA)ₙ₋₁—H      III in which i is an integer and 0≦i≦n, or a reactive derivative of this compound, in the presence of a reaction auxiliary if required, in a suitable solvent and under suitable temperature conditions, the compounds II and III optionally being in the form of the reactive derivative of the acid or the amine group and the unreactive groups being protected. The protected groups are freed where appropriate, it being possible for the reactive derivatives of the acids to be halides, for example chloride, or azidoacyl ester anhydride. The protective groups for the acids or for the amine groups are known in the synthesis of peptides.

More particularly, the present invention also relates to a process for the preparation of the compound of formula I, defined in that:
(a) a compound of formula:

IV is reacted with an acid of formula

X—(AA)ₙ—H      V or a reactive derivative of this carboxylic acid, or
(b) a compound of formula:

VI is reacted with a compound of formula:

X—(AA)ₙ₋₁—H      VII or a reactive derivative of this compound, or, if required, in the presence of a reaction auxiliary, in a suitable solvent and under suitable temperature conditions, the compounds VI and VII if required being in the form of the reactive derivative of the acid or the amine group and it being possible for the non-reactive groups to be protected.

Thus, in order to attach an amino either directly in position 1 of the piperazine ring, or following one or more amino acids which are already attached, a suitable derivative of the amino acid, the amine group of which is protected, is reacted with a derivative of formula II, IV or VI containing hydrogen at the end of the chain in position 1 of the piperazine ring.

Thus, in order to attach glycine or alanine, a glycinate or alaninate is used, for example N-hydroxysuccinimide N-fluorenylmethyloxycarbonylglycinate.

When the reaction is complete, the amino acid is attached on position 1, the amino group still being protected by the protective group, for example the N-fluorenylmethyloxycarbonyl group. The compound obtained is then deprotected, for example using piperidine.

Other protective group-deprotecting agent systems may, of course, be envisaged.

The attachment reaction is carried out in a suitable solvent, for example ethyl acetate, although other solvents may also be envisaged.

In order to attach a group of the diacyl type, for example succinyl, still on position 1 of the piperazine ring or at the end of the chain attached to the piperazine ring, a compound of formula II, IV or VI as defined above is reacted with a carboxylic acid derivative, especially with an anhydride, succinic anhydride when it is desired to attach a radical of the succinic type, or, when it is desired to attach, for example, an alkanoyl radical, with the corresponding acid anhydride.

The reaction is carried out at ambient temperature, under practically equimolar conditions, and in the presence of a suitable solvent, for example dimethylformamide.

According to another embodiment, for example in order to attach an alkenoyl radical, an acid halide, for example the corresponding acid chloride, is used, in a suitable solvent, the reaction then being carried out in the presence of a reaction auxiliary which is capable of attaching the halide, for example triethylamine and under suitable temperature conditions, i.e. the mixture is cooled in ice at the time of adding the alkenoyl halide in small amounts. The conditions are practically equimolar in this case as well.

Irrespective of the procedure for implementing the process, in order to isolate the products, before or after deprotecting the amino group where appropriate, conventional techniques of evaporating the solvent, washing with water or with other solvents, extraction with other solvents such as chloroform or ether, chromatography or purification on silica gel and/or recrystallization are used.

The invention additionally relates to compounds of formula II, IV or VI as defined above, in the form of intermediates of synthesis for the implementation of the above process.

The compounds of formula II, IV or VI are known especially from European Pat. No. 0,006,722 and French Pat. No. 2,378,778 according to which they can be prepared from known compounds.

The Applicant Company has demonstrated the antibacterial, fungicidal and anti-tumor activity of the compounds according to the invention, as will become apparent in the examples.

For this reason, the present invention also relates to the compounds of formula I and Ia defined above, in the form of new medicaments and by way of bactericidal and/or fungicidal and/or anti-tumor agents.

For this reason, the present invention also relates to bactericidal and/or fungicidal and/or anti-tumor compositions containing at least an effective amount of a compound of formula I, or a salt or one of their stereoisomers, and an acceptable carrier.

In particular, the present invention relates to pharmaceutical compositions containing at least an effective amount of a compound according to the invention, a pharmaceutically acceptable salt of one of its compounds or one of its stereoisomers and a pharmaceutically acceptable carrier.

As will become apparent from the examples, the amino acid-containing derivatives exhibit an activity comparable with or even greater than the known derivatives against fungi (especially the alanine derivative) and against *Staphylococcus aureus* (especially the glycyl derivative).

The succinyl type of derivatives are especially valuable for their instability at an acid pH, a pH which is comparable with that of endosomes and lysosomes.

Among these succinyl derivatives, the diacyl glycerol derivatives, i.e. those in which the succinyl substituent carries, at the end of the chain, a glycerol which itself carries fatty chains are particularly useful because of their high bioavailability.

In fact, the presence of fatty chains enables a good lymphatic resorption to occur. Similarly, the oleyl type of derivatives are strongly resorbed, which gives them a high bioavailability.

Other features and advantages of the invention will become apparent on reading the following examples.

In the entire text which follows, the biradical [4-[2-(2,4-dichlorophenyl)-2-(1H-imidazol-1-ylmethyl)-1,3-dioxolan-4-ylmethoxy]phenyl] will be represented by -[A]-, the compound Cis-1-[A]-piperazine being prepared by the deacetylation of the ketoconazole.

EXAMPLE I

Cis-4-[A]-1-(glycyl)piperazine (compound No. 1)

0.88 g (22.4 mmol) of N-hydroxysuccinimide N-fluorenylmethyloxycarbonylglycinate is added to 1 g (20.4 mmols) of cis-1-[A]-piperazine suspended in 100 ml of ethyl acetate. The solution, which is stirred overnight at ambient temperature, gradually becomes clear. After evaporating the solvent, the product is washed with water and extracted with chloroform. The organic phase is washed with brine, dried over sodium sulphate, filtered and evaporated. The product is purified on silica gel using a 96/4 mixture of chloroform/methanol as the eluent. The pure fractions are combined and the eluent evaporated, resulting in a white solid which is recrystallized in a dichloromethane/hexane mixture. 1.04 g (69%) of cis-4-[A]-1-(N-fluorenylmethyloxycarbonylglycyl)piperazine are thereby isolated.

IR (KBr): $\nu$ (cm$^{-1}$): 3310, 1720, 1650, 1625, 1510, 0.72 g (9.37 mmols) of the above compound are dissolved in 10 ml of piperidine freshly distilled over KOH. The mixture is stirred for 1 h at ambient temperature. The piperidine is evaporated off under vacuum, the white solid obtained is washed several times with ether and purified on an alumina column, using a 9/1 mixture of chloroform/methanol as eluent. The product is then recrystallized in a dichloromethane/ether mixture. 0.41 g (80%) of the compound of the title (No. 1) is thereby isolated.

M.p.: 152° C.

IR(KBr): $\nu$ (cm$^{-1}$): 3360, 3320, 1655, 1510

Mass: m/e: 545 (M+)

EXAMPLE II

Cis-4-[A]-1-(alanyl)piperazine (compound No. 2)

Following the same procedure as that described in Example I, starting with cis-1-[A]-piperazine and N-hydroxysuccinimide N-fluorenylmethyloxycarbonyl alaninate, and after deprotecting the amine group using piperidine, 61% of the compound of the title (No. 2) is isolated.

IR (KBr): $\nu$ (cm$^{-1}$): 3360, 1640, 1510

Mass m/e: 559 (M+)

EXAMPLE III

Cis-4-[A]-1-(N-glycylglycyl)piperazine (compound No. 3)

Following the same procedure as that described in I, starting with compound No. 1 and N-hydroxysuccinimide N-fluorenylmethyloxycarbonyl glycinate, and after deprotecting the amine function using piperidine, 55% of the compound of the title (No. 3) is isolated.

IR (KBr): $\nu$ (cm$^{-1}$): 3320, 1665, 1645, 1510
Mass m/e: 602 (M+)

EXAMPLE IV

Cis-4-[A]-1(succinyl)piperazine (compound No. 4)

0.11 g (1.1 mmol) of succinic anhydride dissolved in 2 ml of dimethylformamide is added to 0.489 g (1 mmol) of cis-1-[A]-piperazine suspended in 10 ml of dimethylformamide, at ambient temperature. The solution is stirred for 2 h at ambient temperature and gradually becomes clear. The solvent is evaporated off under vacuum and the solid obtained is recrystallized in isopropanol. 0.494 g (86.5%) of the compound of the title (No. 4) is thereby isolated.

IR (KBr): 1710, 1650, 1510 cm$^{-1}$
Mass: m/e: decomposition

EXAMPLE V

Cis-4-[A]-1-(N-succinylglycyl)piperazine (compound No. 5)

Following the same procedure as that described in Example IV, starting with compound No. 1 and succinic anhydride, and using dimethylformamide as the solvent, 79% of the compound of the title (No. 5) is isolated.

IR(KBr)$\nu$(cm$^{-1}$): 3345, 1720, 1655, 1630, 1510 cm$^{-1}$
Mass M/e: decomposition

EXAMPLE VI

Cis-4-[A]-1-(N-acetylglycyl)piperazine (compound No. 6)

Following the same procedure as that described in Example IV, starting with compound No. 1 and acetic anhydride, and the solvent being dimethylformamide, 80.7% of the compound of the title (No. 6) is isolated.

Ir(KRr): $\nu$ cm$^{-1}$: 3310, 1645, 1510
Mass: m/e: 587 (M+)

EXAMPLE VII

Cis-4-[A]-1-(oleyl)piperazine (compound No. 7)

2.5 g (5.11 mmol) of cis-1-[A]-piperazine are dissolved in 100 ml of dry chloroform. 0.51 g (5.11 mmol) of triethylamine are added to this solution. The mixture is cooled in ice and 1.67 ml (5.11 mmol) of oleyl chloride are added dropwise. The reaction mixture is then stirred for 2 h at ambient temperature. After evaporating the solvent, the product is purified by chromatography on silica gel using a 9/1 mixture of chloroform/methanol as the eluent. The pure fractions are combined and the eluent evaporated off. 3.2 g (84%) of the compound of the title (No. 7) are isolated in the form of an oil.

IR (Film): $\nu$ (cm$^{-1}$): 1645, 1510
Mass: m/e: 753 (M+)

EXAMPLE VIII

Cis-4-[A]-1-(N-oleylglycyl)piperazine (compound No. 8)

0.035 ml (0.25 mmol) of triethylamine is added to 0.138 (0.25 mmol) of compound No. 1 dissolved in 3 ml of dry chloroform. After cooling the mixture in an ice bath, 0.082 ml (0.25 mmol) of oleyl chloride is added. The solution is then stirred for 1 h at ambient temperature. After evaporating the solvent, the product is purified and separated from the triethylamine hydrochloride by chromatography on silica gel using a 9/1 mixture of chloroform/methanol as the eluent. The pure fractions are combined, the eluent is evaporated and the oil obtained ground in hexane gives a white powder. 0.177 g (86.7%) of the compound of the title (No. 8) is thereby isolated and recrystallized in a dichloromethane/hexane mixture.

IR(KBr): (cm)$^{-1}$: 3340, 1660, 1640, 15106
Mass: m/e 810 (M+)

EXAMPLE IX

Test for the activity of the compounds

The activity of the new derivatives according to the invention was tested in vitro by determining the minimum inhibiting concentration (MIC) of the molecules and their fungicidal (minimum fungicidal concentration MFC) or bactericidal (minimum bactericidal concentration MBC) activity. MFC and MBC are defined as the minimum dose which kills 99.9% of the organisms contained in the inoculum. Two species of yeasts pathogenic to man were used: *Candida albicans* ATCCe 10231 and *Candida tropicalis* ATCC 13803. Two species of bacteria were included in the screening: *Staphylococcus aureus* ATCC 25923 and *Salmonella typhimurium* LT2, strain Demerec. The MIC is determined after culturing overnight in a liquid medium, by the microtitration method in dishes containing 96 wells over a concentration range of 100 $\mu$M to 0.0008 $\mu$M. The inoculum contains 10$^5$ to 10$^6$ organisms/ml. The culture media consist on the one hand of RPMI to which 20% of foetal calf serum (inactivated for one hour at 56°) has been added in order to determine the fungistatic activity and Mueller-Hinton agar in order to determine the bacteriostatic power of the newly synthesized molecules on the other. The MFC and MBC for each of these molecules are obtained by subculturing a sample containing 10$^3$ organisms from each well giving negative results for the growth of the organisms, in a solid medium consisting of YM agar (yeasts) or Mueller-Hinton agar (bacteria) overnight at 37°.

The results are shown in Tables I and II below.

The reference products are Miconazole and Fungizone ® (Amphotericin B).

TABLE I

| COMPOUND | MIC ($\mu$M) | | | |
| --- | --- | --- | --- | --- |
|  | C. albicans | C. tropicalis | S. aureus | S. typhimurium |
| Cis-1-[A]-piperazine | 0.13 | 0.117 | 3.65 | >100 |
| Ketoconazole | 0.053 | 0.049 | 20.44 | >100 |
| No. 1 | 0.16 | 0.119 | 11.98 | |
| No. 2 | 0.006 | 0.006 | | |

TABLE I-continued

|  | MIC (μM) | | | |
|---|---|---|---|---|
|  | C. albicans | C. tropicalis | S. aureus | S. typhimurium |
| No. 3 | 0.48 | 0.48 | | |
| No. 4 | 19.82 | 15.23 | 50.78 | |
| No. 5 | 25 | 25 | 50 | |
| No. 6 | 3.13 | 0.78 | | |
| No. 7 | 10.2 | 8.78 | >100 | >100 |
| No. 8 | 31.25 | 53.13 | | |
| REFERENCE PRODUCTS | | | | |
| Miconazole | 0.048 | 0.78 | 1.56 | |
| Fungizone ® | 0.33 | 0.325 | >100 | >100 |

TABLE II

| COMPOUNDS | MFC (μM) | | | |
|---|---|---|---|---|
|  | C. albicans | C. tropicalis | S. aureus | S. typhimurium |
| Cis-1-[A]-piperazine | 2.35 | 1.58 | 25 | |
| Ketoconazole | 0.22 | 4.88 | 50 >100 | |
| No. 1 | 2.38 | 1.3 | 25 | |
| No. 4 | 25 | 50 | >100 | |
| No. 6 | 6.25 | 12.5 | | |
| No. 7 | 125 | 250 | >100 | |
| No. 8 | 62.5 | >100 | | |
| Fungizone ® | 0.83 | 3.17 | 25 >25 | >100 |

EXAMPLE X

Resorption

100 μmols/0.5 ml of DMSO per 100 g of body weight of either ketoconazole (reference product) or oleylketoconazole (compound No. 7) are administered to rats by the gastric route. The animals are sacrificed with $CO_2$, 1 h after the administration. Blood is sampled by cardiac puncture and centrifuged for 15 minutes at 2000 rpm to obtain the plasma.

A series of dilutions of the plasma samples are prepared in a 0.9% NaCl solution, diluting twice each time. 10 μl are sampled from each dilution and deposited on Whatman paper discs. The discs are placed in Petri dishes containing 15 ml of casitone agar covered with a layer containing 3 ml of a less dense agar mixed with 0.1 ml of an overnight culture of *Candida tropicalis*. After incubating overnight the growth inhibition zones around the disks are measured and compared with a standard curve prepared with ketoconazole under the same conditions.

A plasma concentration corresponding to 0.44 μM of the antifungal product is obtained in the case of the rats receiving ketoconazole and 57.3 μM in the case of the rats injected with oleylketoconazole.

EXAMPLE XI

Effect of ketoconazole derivatives on the in vitro synthesis of steroids and anti-tumor effect The anti-tumor effect of the ketoconazole derivatives on androgen-dependent prostatic cancer is demonstrated below. Ketoconazole and its derivatives reduce the plasma levels of testosterone by inhibiting certain enzymes involved in its biogenesis. Progesterone is a key intermediate in the biogenesis of steroid hormones as it leads especially to estradiol in the ovary and to testosterone in the testicles. The inhibiting power of ketoconazole and its derivatives on the enzyme chain for the biogenesis of steroid hormones may be assessed by measuring the conversion of cholesterol into progesterone. A method of determination which enables this property to be quantified is described below.

Leydig tumor cells from mice (I-10, ATCC No. CCL83) were grown in a HAM's F10 medium to which 15% of horse serum and 2.5% of foetal calf serum were added. These cells have the property of secreting progesterone and a product of reduction of the latter which is no longer metabolized, 20α-hydroxy-4-pregnen-3-one. This secretion of steroids is induced by the addition of cAMP in the form of its dibutyryl ester ($N^6$, $O^{2'}$-dibutyryladenosine 3', 5'-cyclic monophosphate sodium salt monohydrate (Sigma)). The cells are subcultured in 25 $cm^2$ falcon dishes and maintained under $CO_2$ (10%). When these become confluent (±1 mg/ml proteins) the medium is replaced with fresh medium containing dibutyryl-cAMP ($1 \times 10^{-4}$M). After incubating for 1 hour with the cAMP, the ketoconazole or its derivatives are added ($9.4 \times 10^{-7}$M) to the culture medium. After incubating for a further period of 3 hours, the supernatants are collected and will be used for the analysis of steroids by HPLC. The cells are rinsed with PBS (phosphate buffered saline: NaCl 0.15M, KCl 2.7 mM, $Na_2HPO_4$-$KH_2PO_4$ 3 mM pH 7.4) and after treating with DOC (deoxycholic acid), the determination of proteins is carried out by the Lowry method.

For the determination of steroids, 2 ml of the culture medium are brought into contact with 5 ml of ether. The tubes are vortexed for 2 minutes. After freezing the aqueous phases in an isopropanol/solid carbon dioxide bath, the ether phase is collected and the ether is evaporated off under a stream of nitrogen at 30° C. The dry extract is then diluted in 150 μl of water and 150 μl of acetonitrile and centrifuged at 13,000 rpm for 10 minutes. 30 μl of the supernatant are injected into HPLC on a 4 mm diameter, 30 cm long μBondapack C18 column (WATERS). The mobile phase consists of 38% of water, 31% acetonitrile and 31% methanol. The flowrate is 2 ml/min and readings are taken at 245 nm.

TABLE 3

| Compound | Progesterone | | 20α-OH-4-pregnen-3-one | |
|---|---|---|---|---|
|  | (1) | (2) | (1) | (2) |
| Ketoconazole | 1878 | 53 | 1296 | 74 |
| Cis-1-[A]-piperazine | 2783 | 78 | 1461 | 84 |

TABLE 3-continued

| Compound | Progesterone (1) | Progesterone (2) | 20α-OH-4-pregnen-3-one (1) | 20α-OH-4-pregnen-3-one (2) |
|---|---|---|---|---|
| No. 2 | 1939 | 55 | 1299 | 74 |
| No. 7 | 2754 | 78 | 1497 | 86 |
| No. 9 | 2231 | 63 | 1725 | 99 |
| No. 10 | 323 | 9 | 605 | 35 |
| Control (+ AMP) | 3546 | 100 | 1744 | 100 |
| Basal (− AMP)* | 554 | — | 785 | — |

(1) ng of steroids/mg of cell proteins/4 hours
(2) % enzyme activity relative to control, i.e. cells induced by cAMP, but in the absence of the inhibitor
*Basal state is that obtained from the cells when not induced by cAMP.

Cis-4-[A]-1-(leucyl)piperazine (compound No. 9)

Following the same procedure as that described in Example I, starting with cis-1-[A]-piperazine and N-hydroxysuccinimide N-fluorenylmethyloxycarbonyl-leucinate and after deprotecting the amine group using piperidine, 55% of the compound of the title (No. 9) is isolated.

IR(KBr): ν (cm$^{-1}$): 3360, 1640, 1510

Cis-4-[A]-1-(phenylalanyl)piperazine (compound No. 10)

Following the same procedure as that described in Example 1, starting with cis-1-[A]-piperazine and N-hydroxysuccinimide N-fluorenylmethoxycarbonyl-phenylalaninate and after deprotecting the amine group using piperidine, 33% of the compound of the title (No. 10) is isolated.

IR (KBr): ν (cm$^{-1}$): 3360, 1640, 1510
Mass: (DCI/acetone): 636 (M$^+$+1)

We claim:
1. Compounds of the formula:

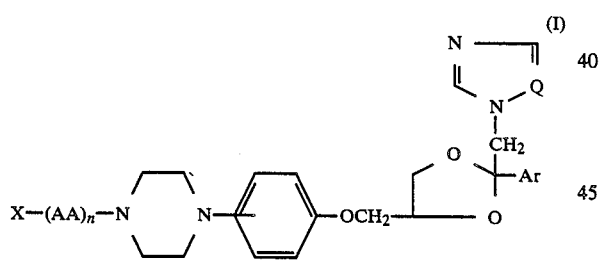
(I)

in which
Q is N or CH;
Ar is a member selected from the group consisting of phenyl and substituted phenyls having from one to three substituents, each substituent being independently selected from the group consisting of halo, lower alkyl and lower alkoxy groups;
—AA— is a divalent radical of a natural amino acid forming part of the structure of proteins or a diacyl radical originating from a substituted or unsubstituted alkanedioic or alkenedioic diacid containing from 3 to 10 carbon atoms wherein when —AA— is a divalent radical of a natural amino acid having an additional functional group selected from the group consisting of —OH, —NH$_2$ and —COOH, said additional functional group may be protected or unprotected, and wherein when —AA— is a divalent radical of an amino acid, the divalent radical —AA— is attached to the piperazine radical

at its C-terminal end;
n is an integer from 0 to 4 inclusive; and
X is H, OH, Y,

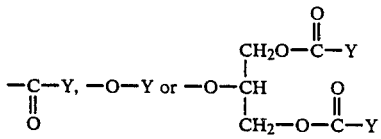

in which
when n is equal to 1, 2, 3 or 4, Y is then a hydrocarbon radical selected from the group consisting of alkyl, alkenyl and alkynyl groups having from 1 to 20 carbon atoms, and
when n is equal to 0, Y is then a hydrocarbon radical selected from the group consisting of alkyl, alkenyl and alkynyl groups having from 7 to 20 carbon atoms;
and pharmaceutically acceptable salts and isomers of these compounds.

2. The compounds as claimed in claim 1, of formula:

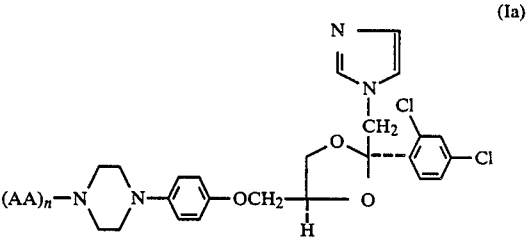
(Ia)

in which
—AA— is a divalent radical of a natural amino acid having the formula

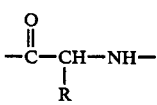

in which R is a substituent in the α position to the amino group of the amino acid, or the diacyl radical

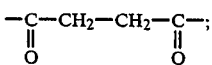

n is an integer from 0 to 4 inclusive;
X is H, Y, $-\underset{\underset{O}{\|}}{C}-Y$, $-OY$ or $-O-\underset{\underset{CH_2O-\underset{\underset{O}{\|}}{C}-Y}{\overset{CH_2O-\overset{\overset{O}{\|}}{C}-Y}{|}}}{CH}$, in which when n is equal to 1, 2, 3 or 4, Y is a hydrocarbon radical selected from the group consisting of alkyl, alkenyl and alkynyl groups having from 1 to 20 carbon atoms, and when n is equal to 0, Y is a hydrocarbon radical selected from the group consisting of alkyl, alkenyl and alkynyl groups having from 7 to 20 carbon atoms;

and their pharmaceutically acceptable salts and isomeric forms.

3. The compounds as claimed in claim 2, in which R represents H or $CH_3$ and their pharmaceutically acceptable salts 4. The compounds as claimed in claim 1, in which $-(AA)_n-X$ has the following meanings:

$-COCH_2NH_2$ $-COCHNH_2$
  $\phantom{-COC}|$
  $\phantom{-COC}CH_3$ $-COCH_2NHCOCH_2NH_2$
$-COCH_2CH_2COOH$
$-COCH_2NHCOCH_2CH_2COOH$
$-COCH_2NHCOCH_3$
$-CO(CH_2)_7CH=CH(CH_2)_7CH_3$
$-COCH_2NHCO(CH_2)_7CH=CH(CH_2)_7CH_3$.

and their pharmaceutically acceptable salts.

5. Bactericidal and/or fungicidal and/or anti-cancer compositions containing at least a bactericidal and/or fungicidal and/or anti-cancer effective amount of a compound as claimed in claim 1 or an acid addition salt or one of their stereoisomers, and an acceptable carrier.

* * * * *